United States Patent
Nishiyama et al.

(10) Patent No.: US 6,323,348 B1
(45) Date of Patent: Nov. 27, 2001

(54) PROCESS FOR PRODUCING CYCLOALKYL [B]BENZOFURANS

(75) Inventors: Hisao Nishiyama, Toyohashi; Hisanori Wakita, Chigasaki; Hiroshi Nagase, Kamakura, all of (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 09/423,827

(22) PCT Filed: Mar. 17, 1999

(86) PCT No.: PCT/JP99/01303

§ 371 Date: Feb. 14, 2000

§ 102(e) Date: Feb. 14, 2000

(87) PCT Pub. No.: WO99/47509

PCT Pub. Date: Sep. 23, 1999

(30) Foreign Application Priority Data

Mar. 18, 1998 (JP) .................................... 10-069000

(51) Int. Cl.$^7$ ........................ C07D 307/93; C07D 307/92
(52) U.S. Cl. ............................................. 549/458
(58) Field of Search ............................... 549/458

(56) References Cited

PUBLICATIONS

Lee et al, Ball. Korean Chem. Soc. (1996), 17(10) p. 955–958, "Conformational Effects on the Palladium–Mediated Tandem Alkene Insertion Reaction".*

* cited by examiner

*Primary Examiner*—Alan L. Rotman
*Assistant Examiner*—Raymond Covington
(74) *Attorney, Agent, or Firm*—Birch, Stewart, Kolasch & Birch, LLP

(57) ABSTRACT

The present invention provides a process for producing an optically active compound of cycloalkyl[b]benzofuran using a readily available optically active compound as a starting material by a reaction using a transition metal or the Mitsunobu reaction, or a combination thereof, followed by a cyclization reaction using a metal or an organometallic reagent.

The process can exclude the needs of complicated optical resolution steps as well as enzyme reactions that requires a large amount of solvent and long reaction time besides repeatability is hardly obtained, providing a very useful production process that can apply for not only laboratory preparation but also for industrial scale productions.

3 Claims, No Drawings

PROCESS FOR PRODUCING CYCLOALKYL [B]BENZOFURANS

This application is the national phase under 35 U.S.C. §371 of PCT International Application No. PCT/JP99/01303 which has an International filing date of Mar. 17, 1999, which designated the United States of America.

TECHNICAL FIELD

The present invention relates to a novel process for producing 3a, 8b-cis-dihydro-3H-cyclopenta[b]benzofuran to be used for a starting material for producing 5,6,7-trinor-4,8-inter-m-phenylene PGI2 derivatives that are useful for, for example, medicines, especially for anti-thrombotic agents, and especially to optically active compounds thereof.

BACKGROUND ART

Optically active compounds of 3a, 8b-cis-dihydro-3H-cyclopenta[b]benzofuran derivatives as one of cycloalkyl[b]benzofuran have been obtained by optical resolution of [7-bromo-3a, 8b-cis-dihydoro-3H-cyclopenta[b]benzofuran-5-il] formate using an optically active amine (Japanese Unexamined Patent Publication No. 59-161371), or by optical resolution of an intermediate compound with an enzyme (J. Chem. Soc., Chem. Commun. 811, 1995). However, the procedure becomes complicated since recrystallization is repeated by forming a complex in the optical resolution method using an optically active amine. In the optical resolution method using an enzyme, on the other hand, a dilute substrate concentration is used besides requiring a long reaction time. In addition, repeatability may be sometimes poor depending on the lot of the enzyme used.

The object of the present invention, based on the drawbacks of the conventional art, is to provide a useful process for producing desired optically active cycloalkyl[b]benzofuran by a cyclization reaction using a readily available optically active starting material.

DISCLOSURE OF INVENTION

The present invention provides a process for producing cycloalkyl[b]benzofuran represented by a general formula (II):

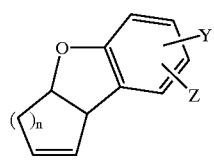

(II)

(in the formula, n is an integer in the range of 0 to 4, and Y and Z independently denote hydrogen, halogen, an alkyl group with a carbon number of 1 to 5, a cycloalkyl group with a carbon number of 3 to 8, a cycloalkylalkyl group with a carbon number of 4 to 9, a cycloalkenylalkyl group with a carbon number of 5 to 10, an aralkyl group with a carbon number of 7 to 12, an alkenyl group with a carbon number of 2 to 7, or an aryl group with a carbon number of 6 to 11) using a compound represented by a general formula (I) as a starting material:

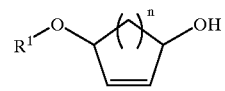

(I)

(in the formula, $R^1$ denotes an acyl group with a carbon number of 1 to 12, an aroyl group with a carbon number of 7 to 15 or $CO_2R^2$ group (wherein $R^2$ represents a linear or branched alkyl group with a carbon number of 1 to 12, a cycloalkyl group with a carbon number of 3 to 8, or an aryl group with a carbon number of 6 to 11), and n is the same as defined above).

In more detail, the present invention provides a process for producing an optically active compound of cycloalkyl[b]benzofuran represented by a general formula (IV):

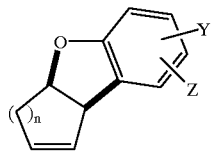

(IV)

(in the formula, n, Y and Z are the same as defined above) or a general formula (VI):

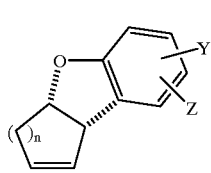

(VI)

(in the formula, n, Y and Z are the same as defined above) wherein the compound represented by the general formula (IV) or (VI) is synthesized by converting the optically active compound represented by the general formula (III)

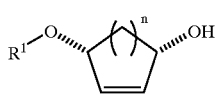

(III)

(in the formula, $R^1$ and n are the same as defined above) as a starting material into a compound represented by a general formula (V)

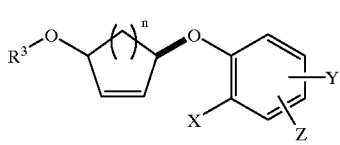

(V)

(in the formula, n, Y and Z are the same as defined above, and $R^3$ denotes a linear or branched alkyl group with a carbon number of 1 to 12, an aralkyl group with a carbon number of 7 to 12, a linear or branched alkylsulfonyl group with a carbon number of 1 to 12, an arylsulfonyl group with a carbon number of 6 to 12, or R⁵ (wherein R⁵ denotes an aryl group with a carbon number of 6 to 11), X denotes halogen), or a general formula (VII):

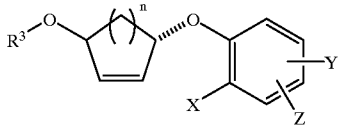

(VII)

(in the formula, R³, n, X, Y and Z are the same as defined above) by a reaction using a transition metal, the Mitsunobu reaction, or a combination thereof, and cyclizing the compound represented by the general formula (V) or the general formula (VII) using a metallic reagent or an organometallic reagent.

The present invention also provide a compound that is useful in the process for producing cycloalkyl[b]benzofuran represented by a general formula (VIII):

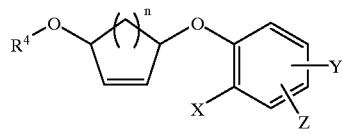

(VIII)

(in the formula, R⁴ denotes hydrogen, an acyl group with a carbon number of 1 to 12, an aroyl group with a carbon number of 7 to 15, a linear or branched alkyl group with a carbon number of 1 to 12, an aryl group with a carbon number of 6 to 11, an aralkyl group with a carbon number of 7 to 12, a linear or branched alkylsulfonyl group with a carbon number of 1 to 12, an arylsulfonyl group with a carbon number of 6 to 12, or CO₂R² (wherein R² denotes a liner or branched alkyl group with a carbon number of 1 to 12, a cycloalkyl group with a carbon number of 3 to 8, or an aryl group with a carbon number of 6 to 11), n denotes an integer in the range of 0 to 4. X denotes halogen, and Y and Z independently denote hydrogen, halogen, an alkyl group with a carbon number of 1 to 5, a cycloalkyl group with a carbon number of 3 to 8, a cycloalkylalkyl group with a carbon number of 4 to 9, a cycloalkenylalkyl group with a carbon number of 5 to 10, an aralkyl group with a carbon number of 7 to 12, an alkenyl group with a carbon number of 2 to 7, and an aryl group with a carbon number of 6 to 11 (excluding the compound in which both of Y and Z denote hydrogen, or one of them denotes hydrogen and the other denotes an alkenyl group with a carbon number of 3, when R⁴ denotes hydrogen and X denotes iodine.))

BEST MODE FOR CARRYING OUT THE INVENTION

A production process of the optically active compound (IV) is illustrated in Scheme 1:

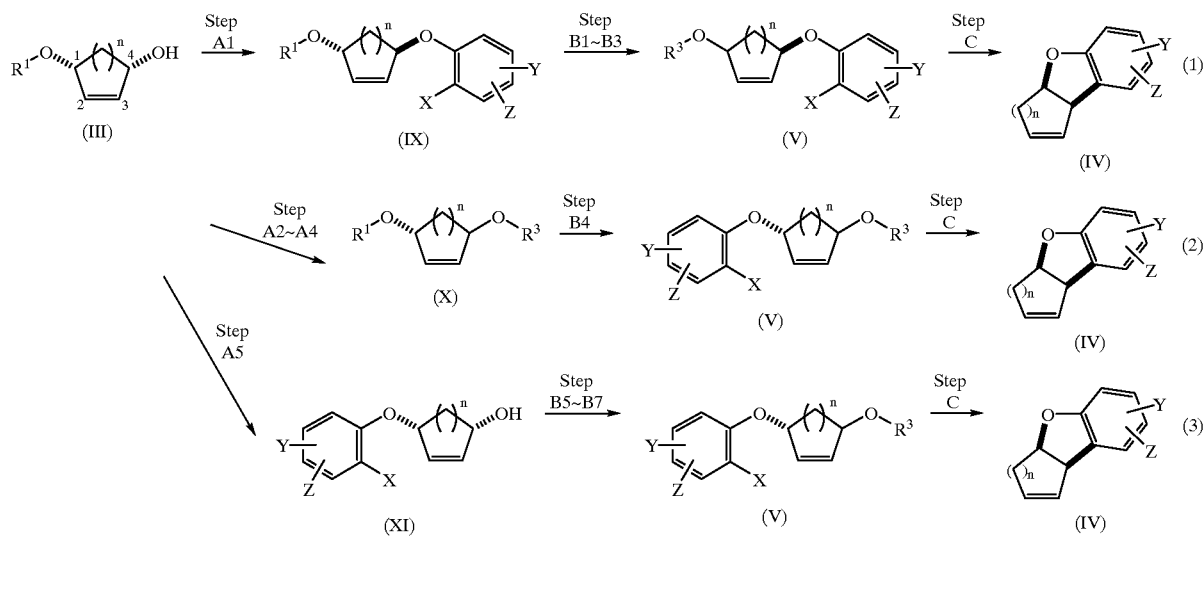

Scheme 1

(in the formula, R¹, R³, n, X, Y and Z are the same as defined above.)

It is preferable that R¹ is an acyl group with a carbon number of 1 to 5, an aroyl group with a carbon number of 7 to 10 or CO₂R² (wherein R² denotes a linear or branched alkyl group with a carbon number of 1 to 5). R³ preferably denotes a linear or branched alkyl group with a carbon number of 1 to 5, an aralkyl group with a carbon number of 7 to 10, a linear or branched alkylsulfonyl group with a carbon number of 1 to 5, an arylsulfonyl group with a carbon number of 6 to 10, or R⁵ (wherein R⁵ denotes an aryl group with a carbon number of 6 to 9). The integer n is preferably 1 or 2. X preferably represents chlorine, bromine or iodine, but bromine or iodine is most preferable among them. It is preferable that Y and Z independently represent hydrogen, chlorine, bromine or an alkyl group with a carbon number of 1 to 5.

The optically active compound (III) to be used as a starting material can be synthesized by a method known in the art (Carl R. Johnson and Scott J. Bis, Tetrahedron Letters, 1992, 33, 728). In more detail, it is preferable to use (1S, 4R)-cis-4-acetoxy-2-cyclopenten-1-ol, (1S, 4R)-cis-4-benzoyloxy-2-cyclopenten-1-ol or (1S, 4R)-cis-4-ethoxycarbonyloxy-2-cyclopenten-1-ol as a starting material, (1S, 4R)-cis-4-acetoxy-2-cyclopenten-1-ol being most preferable among them. The commercially available (1S, 4R)-cis-4-acetoxy-2-cyclopentene-1-ol may be used.

The formula (1) in Scheme 1 represents a synthetic route by which, after a stereochemical inversion reaction by substituting the 4-hydroxy group in the compound (III) with an o-halogenated phenol compound in the step A1, the compound (V) is obtained by converting $R^1$ into a functional group by the steps B1 to B3 to obtain the compound (IV) by a cyclization reaction.

The formula (2) in Scheme 2 represents a synthetic route by which, after converting the 4-hydroxy group in the compound (III) into a functional group in the steps A2 to A4, the 1-$R^1O$ group is substituted with an o-halogenated phenol derivative to form the compound (V) while maintaining its stereochemical configuration in the step B4, followed by a cyclization reaction to obtain the compound (IV).

The formula (3) in Scheme 1 represents a synthetic route by which, after substituting the 1-$R^1O$ group in the compound (III) with an o-halogenated phenol derivative while maintaining its stereochemical configuration in the step A5, the compound (V) is obtained by converting the 4-hydroxy group into a functional group, followed by a cyclization reaction to obtain the compound (IV).

Individual steps in Scheme 1 will be described in detail hereinafter. Firstly, details of the formula (1) is shown in Scheme 2.

boxylate or diisopropyl azodicarboxylate, and a phosphorus reagent such as triphenyl phosphine triphenylphosphine or tributyl phosphine tributylphosphine are used in the Mitsunobu reaction. Diethyl azodicarboxylate and triphenyl phosphine are preferably used as the azo-compound and phosphorous reagent among them. While ether solvents such as tetrahydrofuran, dioxane or diethyl ether, or aromatic solvents such as benzene or toluene may be used, it is preferable to use tetrahydrofuran or benzene. The reaction temperature is in the range of −50 to 100° C., a temperature range of −5 to 30° C. being preferable. The reaction time is in the range of 5 minutes to 50 hours, usually 30 minutes to 5 hours.

The step B1 comprises hydrolyzing the compound (IX) followed by the Mitsunobu reaction using phenols represented by a general formula $R^5OH$ ($R^5$ is the same as defined above) to obtain the compound (XIII). The compound (IX) is hydrolyzed by allowing it to react with a base in a hydrous alcohol such as hydrous methanol or ethanol, or in a hydrous ether such as hydrous dioxane or tetrahydrofuran. Bases such as sodium hydroxide, potassium hydroxide, sodium carbonate or potassium carbonate are preferably used. The reaction temperature is in the range of −100 to 100° C., preferably −20 to 50° C. The reaction time is in the range of 5 minutes to 120 hours, usually in the range of 0.5 to 30 hours. Preferable phenol compounds to be used for the Mitsunobu reaction include phenol, cresol or the like, phenol being more preferable. The reaction conditions such as reagents and solvents to be used in the reaction, and the reaction temperature and reaction time are the same as used in the step A1.

The step B2 represents a method by which the compound (IX) is directly converted into the compound (XIV) using a transition metal catalyst without the hydrolyzing step. A

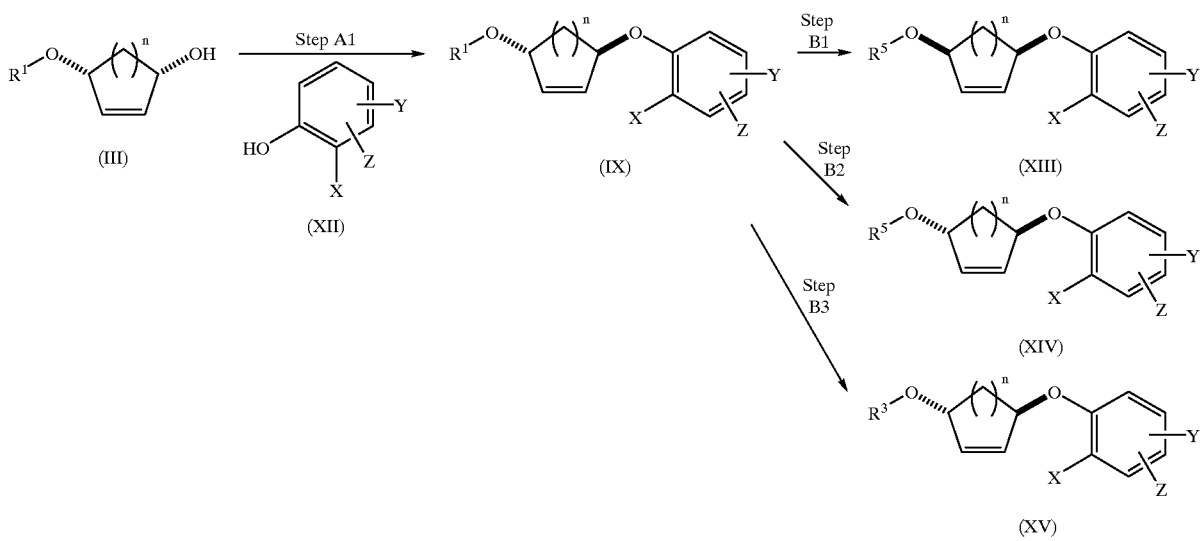

Scheme 2

In the step A1, the compound (IX) is obtained by the Mitsunobu reaction of the compound (III) with the compound (XII). An azo-compounds such as diethyl azodicarboxylate or nickel catalyst is used as the transition metal catalyst for this purpose, which is allowed to react with a phenol compound represented by $R^5OH$ ($R^5$ is defined as described above). Although a variety of complexes may be used as the palladium catalyst or nickel catalyst, it is preferable to use $Pd_2(dba)_3/CHCl_3$, $Pd(PPh_3)_4$, $Ni(dppe)_2$ or $Ni(dppp)_2$. The preferable amount of the catalyst used is 0.0001 to 10 equivalent, preferably 0.01 to 2 equivalent. While phenol, cresol or the like is used as the phenol compound, phenol is preferably used. While ether solvents such as tetrahydrofuran, dioxane or diethyl ether, or aprotic polar solvents such as dimethylsulfoxide or acetonitrile may be used for the reaction solvent, tetrahydrofuran is preferably used. The reaction temperature is in the range of −120 to 200° C., preferably in the range of −20 to 50° C. The reaction time is in the range of 5 minutes to 50 hours, usually in the range of 30 minutes to 10 hours.

In the step B3, after hydrolyzing the compound (IX), the hydroxyl group formed is converted into a functional group of $R^3O$ group ($R^3$ is the same as defined above). The reaction conditions such as the base and solvent to be used in the hydrolysis reaction, and the reaction temperature and reaction time are the same as in the hydrolysis reaction in the Step B1. The compound (XV) is obtained for the succeeding functional group conversion reaction of the hydroxy group by allowing a halogenated alkyl, halogenated aralkyl, halogenated alkylsulfonyl or halogenated arylsulfonyl group to react in the presence of a base. While benzyl bromide, iodo methane, methanesulfonylchloride, p-toluenesulfonyl chloride or the like is actually used, it is preferable to use benzyl bromide. The bases to be used include amine bases such as triethylamine, pyridine or the like, sodium hydride, potassium hydride or the like. The solvents to be used include halogenate solvents such as methylene chloride, ether based solvents such as tetrahydrofuran, and aprotic polar solvents such as dimethylformamide. The reaction temperature is in the range of −100 to 100° C., preferably in the range of −20 to 50° C. The reaction time is in the range of 5 minutes to 50 hours, usually 30 minutes to 10 hours.

In the step C, a cyclizaton reaction is carried out using a metallic or organometallic reagent to obtain optically active cycloalkyl[b]benzofuran (IV). While ether solvents such as diethyl ether, tetrahydrofuran, 1,2-dimethoxyethane, dioxane or the like is used, tetrahydrofuran is a preferable solvent among them.

For the cyclization reaction using a metal, the compound (V) may be directly converted into a Grignard reagent with metallic magnesium, or the compound (V) may be converted into an organic lithium compound with metallic lithium. When the compound is cyclized with an organometallic compound, the organic lithium compound and Grignard reagent to be used for the reaction. Preferably, methyllithium, n-butyllithium, phenyllithium, cyclohexylmagnesium chloride or n-butylmagnesium bromide is used. The reaction temperature is in the range of −120 to 100° C., preferably in the range of −78 to 50° C. The reaction time is in the range of 5 minutes to 120 hours, usually in the range of 30 minutes to 5 hours.

The compound (IV) is usually isolated by distillation, silica gel chromatography or recrystallization.

Details of the formula (2) is described in Scheme 3.

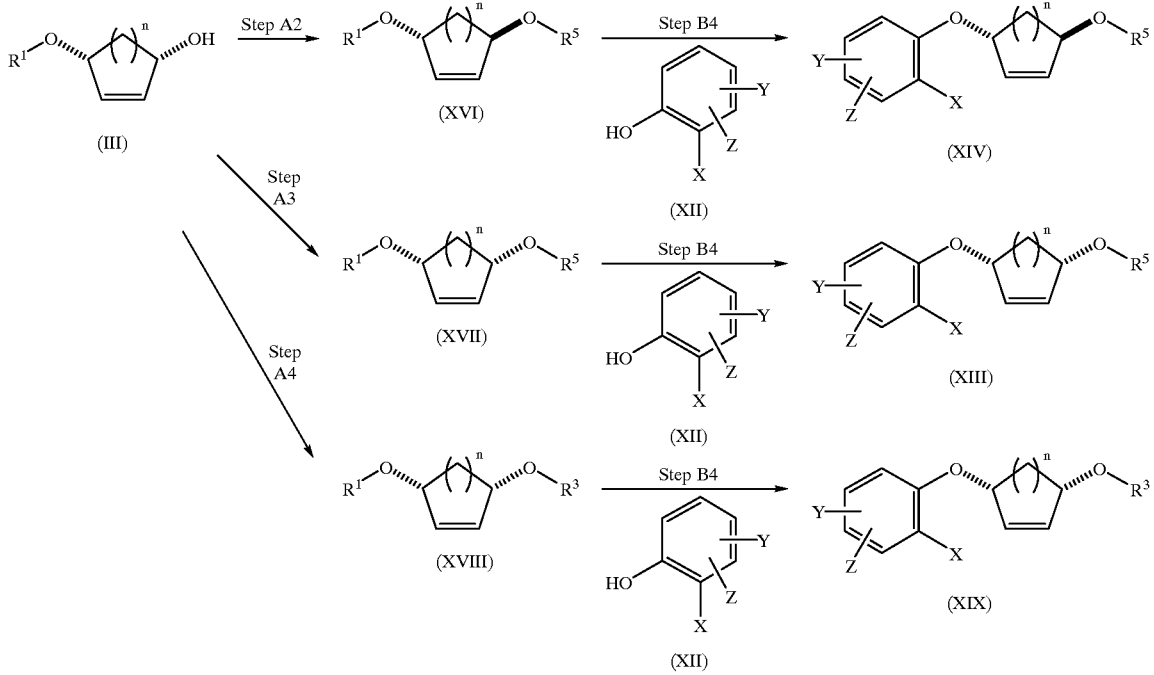

Scheme 3

In the step A2, the compound (XVI) is obtained by the Mitsunobu reaction using compound (III) and phenol compounds represented by the general formula $R^5OH$ ($R^5$ is the same as defined above). While phenol, cresol or the like is used as the phenol compounds, phenol is preferable. The reaction conditions such as the reagents and solvents to be used in the reaction, and the reaction temperature and reaction time are the same as used in the step A1.

In the step A3, a carbonate ester is formed by converting the hydroxy group by allowing dialkyl carbonate or halogenated alkyl formate to react with the compound (III) in the ditions such as catalysts and solvents to be used in the reaction, and the reaction temperature and reaction time are the same as used in the step B2.

The step C is the same as described previously.

Details of the formula (3) are illustrated in Scheme 4.

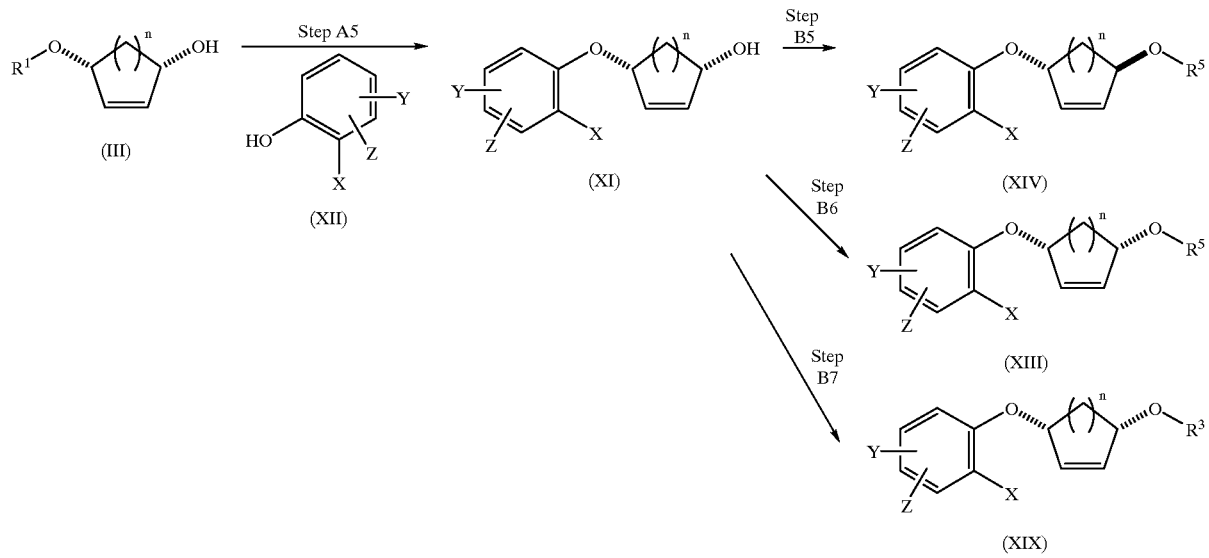

Scheme 4 presence of a base. It is preferable to use pyridine, dimethylaminopyridine, triethylamine or the like as the base. Dimethyl carbonate, diethyl carbonate or the like is used as the dialkyl carbonate. Methyl chloroformate, ethyl chloroformate or the like is used as the halogenated alkyl formate. While a halogenated solvent such as methylene chloride, an aromatic solvent such as benzene or an ether solvent such as tetrahydrofuran is used for the reaction solvent, methylene chloride or tetrahydrofuran is preferable among them. Reaction temperature is in the range of −100 to 100° C., preferably in the range of −20 to 50° C. The reaction time is in the range of 5 minutes to 100 hours, usually 30 minutes to 50 hours. The compound (XVII) is obtained by allowing the above product to react with a phenol compound represented by the general formula $R^5OH$ ($R^5$ is the same as defined above) in the presence of the palladium catalyst or nickel catalyst. The reaction conditions such as phenols, catalysts, reagents and solvents to be used in the reaction, and the reaction temperature and reaction time are the same as used in the step B2.

In the step A4, the compound (XVIII) is obtained by converting the hydroxy group of the compound (III) into a functional group. The reaction conditions such as the reagents, bases and solvents to be used in the reaction, and the reaction temperature and reaction time are the same as used in the step B3.

In the step B4, the compound (XIV), (XIII) or (XIX) is obtained by allowing the compound (XVI), (XVII) or (XVIII) to react with the compound (XII) in the presence of the palladium catalyst or nickel catalyst. The reaction con- In the step A5, the compound (XI) is obtained by allowing the compound (III) to react with the compound (XII) in the presence of the palladium catalyst or nickel catalyst. The reaction conditions such as catalysts and solvents to be used in the reaction, and the reaction temperature and reaction time are the same as used in the step B2.

In the step B5, the compound (XIV) is obtained by the Mitsunobu reaction using the compound (XI) and a phenol compound represented by the general formula $R^5OH$ ($R^5$ is the same as defined above). While phenol, cresol or the like may be used as the phenol compound, phenol is preferably used. The reaction conditions such as reagents and solvents to be used in the reaction, and the reaction temperature and reaction time are the same as used in the step A1.

In the step B6, after converting the hydroxyl group of the compound (XI) to form a carbonate ester, the product is allowed to react with a phenol compound represented by the general formula $R^5OH$ ($R^5$ is the same as defined above) in the presence of the palladium catalyst or nickel catalyst to obtain the compound (XIII). The reaction conditions such as reagents, bases, catalysts and solvents to be used in the reaction, and the reaction temperature and reaction time are the same as used in the step A3.

In the step B7, the compound (XIX) is obtained by converting the hydroxy group of the compound (XI) into functional group. The reaction conditions such as reagents, bases and solvents to be used in the reaction, and the reaction temperature and reaction time are the same as used in the step B3.

The step C is the same as described previously.

The production process of the optically active compound (VI) is illustrated in Scheme 5.

Scheme 5

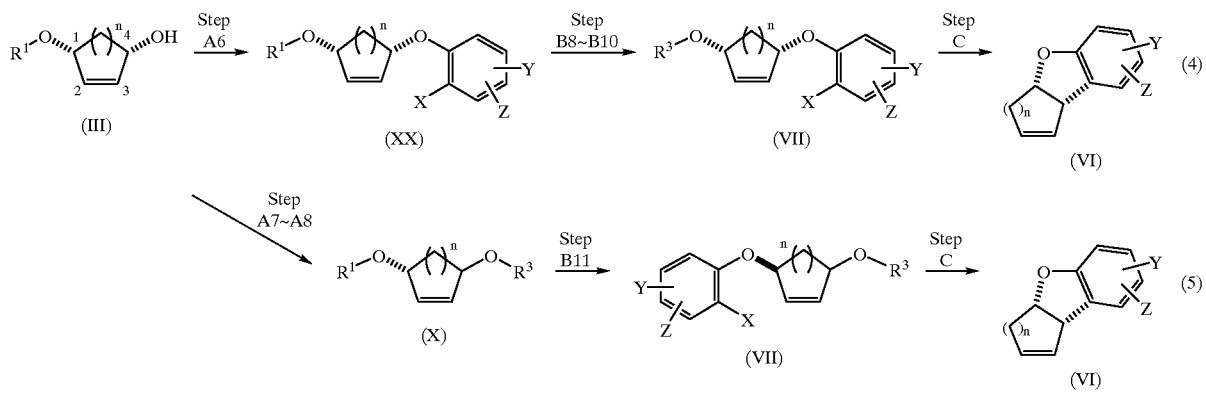

(in the formula, $R^1$, $R^3$, n, X, Y, and Z are the same as defined above)

Scheme 6

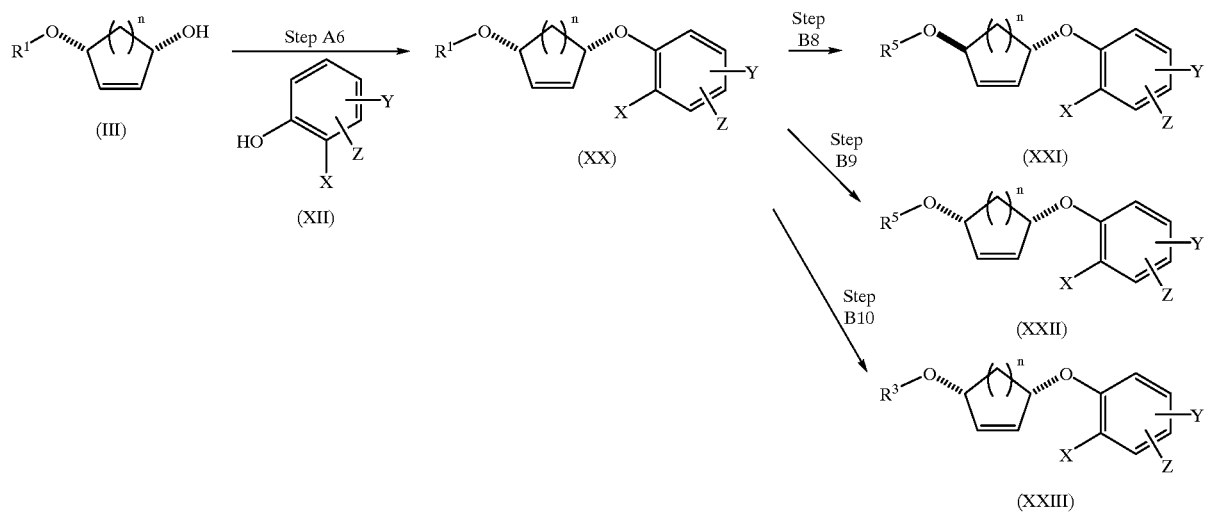

The formula (4) in Scheme 5 denotes a synthetic route comprising: in the step A6, substituting the 4-hydroxy group of the compound (III) with an o-halogenated phenol derivative while maintaining the stereochemical configuration of the compound (III); forming the compound (VII) by converting $R^1$ into a functional group through the steps of B8 to B10; and obtaining the compound (VI) by a cyclization reaction.

The formula (5) in Scheme 5 denotes a synthetic route comprising: in the steps A7 and A8, converting the 4-hydroxy group of the compound (III) into a functional group, substituting the functional group with an o-halogenated phenol derivative while inverting the stereochemical configuration to form the compound (VII) in the step B11; and obtaining the compound (VI) by a cyclization reaction.

Individual steps in Scheme 5 are described in detail below. Details of the formula (4) are illustrated in Scheme 6.

In the step A6, the hydroxy group in the compound (III) is at first converted into a carbonate ester. Then, the carbonate ester is allowed to react with the compound (XII) in the presence of the palladium catalyst or nickel catalyst to obtain the compound (XX). The reaction conditions such as reagents, bases, catalysts and solvents to be used in the reaction, and the reaction temperature and reaction time are the same as used in the step A3.

In the step B8, the compound (XXI) is obtained by the Mitsunobu reaction using a phenol compound represented by the general formula $R^5OH$ ($R^5$ is the same as defined above) after hydrolyzing the compound (XX). The reaction conditions such as reagents, bases and solvents to be used in the reaction, and the reaction temperature and reaction time are the same as used in the step B1.

In the step B9, the compound (XXII) is obtained by allowing the compound (XX) to react with a phenol compound represented by the general formula $R^5OH$ ($R^5$ is the same as defined above) in the presence of the palladium catalyst or nickel catalyst. The reaction conditions such as reagents, catalysts and solvents to be used in the reaction, and the reaction temperature and reaction time are the same as used in the step B2.

In the step B10, the compound (XXIII) is obtained by converting the hydroxy group in the compound (XX) formed by hydrolysis into a functional group. The reaction conditions such as reagents, bases and solvents to be used in the reaction, and the reaction temperature and reaction time are the same as used in the step B3.

The step C is the same as described previously.
The formula (5) is illustrated in detail in Scheme 7.

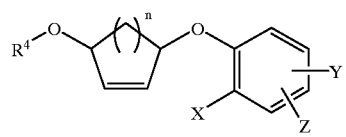

(in the formula, $R^4$ denotes hydrogen, an acyl group with a carbon number of 1 to 12 or an aroyl group with a carbon number of 7 to 15, a linear or branched alkyl group with a carbon number of 1 to 12, an aryl group with a carbon number of 6 to 11, an aralkyl group with a carbon number Scheme 7

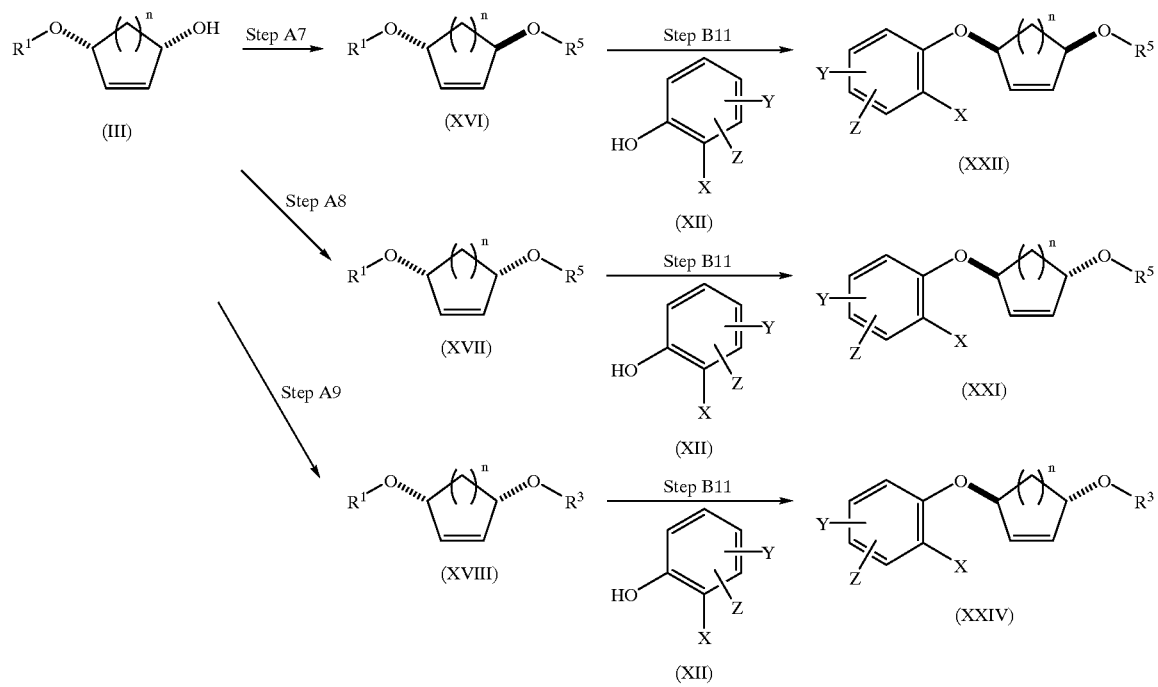

The steps A7, A8 and A9 are the same as described in the steps A2, A3 and A4.

In the step B11, the compounds (XXII), (XXI) or (XXIV) is obtained by the Mitsunobu reaction with the compound (XII) after hydrolyzing the compounds (XVI), (XVII) or (XVIII). The reaction conditions such as reagents, bases and solvents to be used in the reaction, and the reaction temperature and reaction time are the same as used in the step B1.

The step C is the same as described previously.

A compound having an inverse stereochemical configuration can be obtained by the production methods illustrated in Scheme 1 and Scheme 5 when an enantiomer of the compound (III) is used instead of the compound (III). Actually, the compound (VI) is obtained by the method in Scheme 1 while the compound (IV) is obtained by the method in Scheme 5. When a racemic compound is used as the starting material, a racemic product is obtained.

Among the compounds represented by the general formula (VIII) that are useful in producing cycloalkyl[b]benzofuran, of 7 to 12, a linear or branched alkylsulfonyl group with a carbon number of 1 to 12, an arylsulfonyl group with a carbon number of 6 to 12, or $CO_2R^2$ (wherein $R^2$ denotes a linear or branched alkyl group with a carbon number of 1 to 12, a cycloalkyl group with a carbon number of 3 to 8, or an aryl group with a carbon number of 6 to 11), n denotes an integer in the range of 0 to 4, X denotes halogen, and Y and Z independently denote hydrogen, halogen, an alkyl group with a carbon number of 1 to 5, a cycloalkyl group with a carbon number of 3 to 8, a cycloalkylalkyl group with a carbon number of 4 to 9, a cycloalkenylalkyl group with a carbon number of 5 to 10, an aralkyl group with a carbon number of 7 to 12, an alkenyl group with a carbon number of 2 to 7, and an aryl group with a carbon number of 6 to 11 (excluding the compound in which both of Y and Z denote hydrogen, or one of them denotes hydrogen and the other denotes an alkenyl group with a carbon number of 3 when $R^4$ denotes hydrogen and X denotes iodine)), the compound, in which $R^4$ is hydrogen, an acyl group with a carbon number of 1 to 5, an aroyl group with a carbon number of 7 to 10, a linear or branched alkyl group with a carbon number of 1 to 5, an aryl group with a carbon number of 6 to 9, an aralkyl group with a carbon number of 7 to 10, a linear or branched alkylsulfonyl group with a carbon number of 1 to 5, or an arylsulfonyl group with a carbon number of 6 to 10, wherein n denotes an integer of 1 or 2, X denotes chlorine, bromine or iodine, and Y and Z independently denote hydrogen, chlorine, bromine or an alkyl group with a carbon number of 1 to 5, is preferable.

The present invention enabled an optically active compound of cycloalkyl[b]benzofuran to be produced using a readily available optically active starting material. The production process according to the present invention can exclude the needs of complicated optical resolution steps as well as enzyme reactions that require a large amount of solvents and long reaction time besides repeatability is hardly obtained, providing a very useful production process that can apply for not only laboratory preparations but also for industrial scale productions.

The present invention will be described in more detail below with reference to examples.

EXAMPLE

Example 1

Synthesis of (1R, 4R)-trans-1-o-bromophenoxy-4-acetoxy-2-cyclopentene (1)

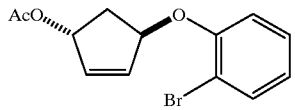

(1)

A 20 mL round-bottom flask was charged with 300 mg (2.11 mol, m.w.=142.16) of commercially available (1S, 4R)-cis-4-acetoxy-2-cyclopentene-1-ol and 1.660 g (6.33 mol, m.w.=262.29) of triphenylphosphine and evacuated, followed by purging with argon. The compounds were dissolved in benzene (6 ml) under nitrogen. To the resulting solution was added 489.3 μL (4.22 mmol, m.w.=173.01, d=1.492) of o-bromophenol and 996.8 μL (6.33 mmol, m.w.=174.16, d=1.106) of diethyl azodicarboxylate dissolved in benzene (3 mL) dropwise and the mixture was stirred at room temperature for 2 hrs. Progress of the reaction was checked by TLC (hexane/ethyl acetate=3/1, Rf of the objective compound=0.44, Rf of the starting material=0.08). The reaction mixture was concentrated in vacuo and then a saturated aqueous solution (20 mL) of sodium hydrogen carbonate was added. The aqueous layer was extracted with ether (20 mL×2) and the organic layer was washed with an aqueous solution (20 mL) of oxalic acid. The organic layer was further washed with 0.5N aqueous sodium hydroxide solution (20 mL) by cooling with ice and then washed with a saturated aqueous solution (5 mL) of sodium hydrogen carbonate. The organic layer was dried over anhydrous sodium sulfate and filtrated, followed by concentration in vacuo. Purification on silica gel column chromatography ($SiO_2$=50 g, eluent: hexane/ether=10/1) afforded 566.5 mg (1.91 mmol, m.w.=297.15, yield; 90.4%) of the desired product (1) as an oil.

$^1$H NMR (270 MHz, $CDCl_3$, TMS): δ2.06 (s, 3H), 2.28 to 2.37 (m, 1H), 2.42 to 2.51 (m, 1H), 5.49 (brd, 1H), 5.87 (m, 1H), 6.20 (d, J=6.9 Hz, 1H), 6.28 (d, J=4.9 Hz, 1H), 6.85 (t, J=6.4 Hz, 7.3 Hz, 1H), 6.92 (d, J=8.3 Hz, 1H), 7.25 (t, J=2.0 Hz, 9.0 Hz, 1H), 7.55 (d, J=7.3 Hz, 1H) ppm IR (NaCl): 3437, 3068, 2944, 1734, 1581, 1475, 1441, 1369, 1240, 1036, 966, 909, 750 $cm^{-1}$ Example 2

Synthesis of (1R, 4R)-trans-1-o-bromophenoxy-2-cyclopentene-4-ol (2)

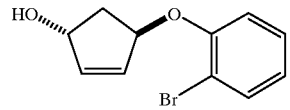

(2)

To a 10 mL round-bottom flask, 80 mg (0.269 mmol, m.w.=297.15) of (1R, 4R)-trans-1-o-bromophenoxy-2-cyclopentene- 4-ol (1) was added and dissolved in ethanol (5 mL). 0.5 mL of 2N aqueous solution of sodium hydroxide (1 mmol, m.w.=40.0) was added and the mixture was stirred overnight at room temperature. Progress of the reaction was checked by TLC (hexane/ethyl acetate=1/1, Rf of the objective compound=0.32, Rf of the starting material=0.73). After the solvent was removed in vacuo, water (5 mL) was added to the residue and extracted with ether (20 mL×2). The organic layer was dried over anhydrous sodium sulfate and filtrated, followed by concentration in vacuo. Purification on silica gel column chromatography ($SiO_2$=10 g, eluent: hexane/ethyl acetate=2/1) afforded 57.8 mg (0.242 mmol, m.w.=239.11, yield; 90.0%) of the desired product (2) as a white solid.

$^1$H NMR (270 MHz, $CDCl_3$, TMS): δ1.60 (d, J=6.4 Hz, 1H), 2.16 to 2.25 (m, 1H), 2.39 to 2.47 (m 1H), 5.15 (brd, 1H), 5.50 (m, 1H), 6.20 (s, 2H), 6.88 (t, J=7.7 Hz, 7.8 Hz, 1H), 6.93 (d, J=8.3 Hz, 1H), 7.26 (t, J=6.4 Hz, 8.9 Hz, 1H), 7.53 (d, J=7.8 Hz, 1H) ppm $^{13}$C NMR (67.9 MHz, $CDCl_3$): δ42.6, 77.5, 79.0, 84.8, 114.5, 116.4, 123.6, 129.9, 134.8, 135.0, 140.9, 156.2 ppm IR (KBr): 3341, 3250, 2904, 2404, 1581, 1475, 1363, 1280, 1239, 1060, 750 $cm^{-1}$ $[\alpha]_D^{23}$: +166° (c 1.00, $CHCl_3$)

Elementary analysis for $C_{11}H_{11}O_2Br$ (F.W. 255.111) Theoretical (%) C: 51.79, H: 4.35 Found (%) C: 51.56, H: 4.45

Example 3

Synthesis of (1R, 4R)-trans-1-o-bromophenoxy-4-benzyloxy-2-cyclopentene (3)

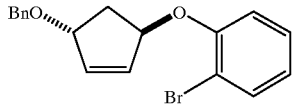

(3)

A 30 mL round-bottom flask was charged with 314 mg (1.31 mmol, m.w.=239.11) of (1R, 4R)-trans-1-o-bromophenoxy-2-cyclopentene-4-ol (2) and evacuated, followed by purging with argon. The compound was dissolved in dimethoxyethane (5.5 mL) under nitrogen, and the solution of 377.3 mg(7.86 mmol, m.w.=24.0, vol 50%) of sodium hydride in dimethoxyethane (6 mL) was added. After bubbling was stopped, 1.56 mL of benzyl bromide (13.13 mmol, m.w.=171.04, d=1.438) was added dropwise and the mixture was stirred at room temperture for 1.5 hr. Progress of the reaction was checked by TLC (hexane/ethyl acetate=6/1, Rf of the objective compound=0.75, Rf of the starting material=0.05). The reaction was quenched with 5 mL of water and the solvent was removed in vacuo and the residue was extracted with ether (20 mL×2). The organic layer was dried over anhydrous sodium sulfate and filtrated, followed by concentration in vacuo. Purification on silica gel column chromatography (SiO$_2$=30 g, eluent: hexane→hexane/ethyl acetate=1/1) afforded 408.4 mg (1.24 mmol, m.w.=329.24, yield 94.5%) of the desired product (3) as an oil.

$^1$H NMR (270 MHz, CDCl$_3$, TMS): δ2.35 (t, J=4.9 Hz, 2H), 4.56 (dd, J=11.7 Hz, 12.2 Hz, 2H), 4.89 (brd, 1H), 5.50 (brd, 1H), 6.23 (dd, J=5.3 Hz, 6.0 Hz, 2H), 6.81 (t, J=7.3 Hz, 7.8 Hz, 1H), 6.93 (d, J=8.3 Hz, 1H), 7.22 to 7.35 (m, 6H), 7.55 (d, J=7.8 Hz, 1H) ppm

Example 4

Synthesis of (3aR, 8bR)-3a, 8b-cis-dihydro-3H-cyclopenta [b]benzofuran (4)

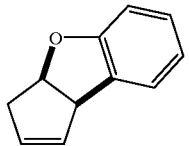

(4)

A Schrenk tube was charged with 164.6 mg (0.5 mmol, m.w.=329.24) of (1R, 4R)-trans-1-o-bromophenoxy-4-benzyloxy-2-cyclopentene (3) and evacuated, followed by purging with argon. THF (2 mL) was added and the mixture was stirred at room temperature under nitrogen. The solution was then cooled to −78° C. or less and 0.364 mL (0.55 mmol, 1.51N hexane solution) of n-BuLi was slowly added with stirring. The reaction mixture was warmed to 0° C. within 1.5 hr (temperature increment of 10° C. in about 13 minutes). Progress of the reaction was checked by TLC (hexane/ether=10/1, Rf of the objective compound=0.68, Rf of the starting material=0.32, TLC plate: Merck 5715). The reaction was quenched with 5 mL of water and the resulting mixture was extracted with ether (7 mL×2). The organic layer was dried over anhydrous sodium salfate and filtrated, followed by concentration in vacuo. Purification on silica gel columun chromatography (SiO$_2$=7 g, eluent: hexane/ether =100/1) afforded 35.4 mg (0.24 mmol, m.w.=158.2, yield 44.8%) of the cyclization product (4) as an oil. The optical yield of cyclization product (4) was determined to 100%ee of R-configuration by chiral gas column chromatography (chiraldex G-TA30 m, column temperature=110° C., injection temperature=135° C., detection temperature=135° C., He pressure=1.5 atm).

$^1$H NMR (270 MHz, CDCl$_3$, TMS): δ2.80 (dd, J=1.5 Hz, 1.5 Hz, 1H), 2.84 (dd, J=1.5 Hz, 5.9 Hz, 1H), 4.38 (d, J=7.3 Hz, 1H), 5.47 (m, 1H), 5.75 (s, 2H), 6.75 (d, J=7.8 Hz, 1H), 6.82 (dd, J=7.3 Hz, 7.3 Hz, 1H), 7.12 (dd, J=7.8 Hz, 7.3 Hz, 1H), 7.20 (d, 7.3 Hz, 1H) ppm

Example 5

Synthesis of (1S, 4R)-cis-1-ethoxycarbonyloxy-4-acetoxy-2-cyclopentene (5)

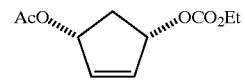

(5)

A 10 mL round-bottom flask was charged with 358.3 mg (2.52 mmol, m.w.=142.16) of commercially available (1S, 4R)-cis-4-acetoxy-2-cyclopentene-1-ol and evacuate, followed by purging with argon. The compound was then dissolved in methylene chloride (7 mL) under nitrogen, 1.90 mL (23.4 mmol, m.w.=79.1, d=0.978) of pyridine and 2.03 µL (14.1 mmol, m.w.=162.14, d=1.12) of diethyl carbonate were added dropwise, followed by adding 31 mg (0.25 mmol, m.w.=122.17) of dimethylaminopyridine and the mixture was stirred at room temperature for 30 hrs. Progress of the reaction was checked by TLC (hexane/ether=1/1, Rf of the objective compound=0.34, Rf of the starting material= 0.04). The reaction mixture was then concentrated in vacuo. Purification on silica gel column chromatography (SiO$_2$ =40 g, eluent: hexane/ether=5/1) afforded 484 mg (2.44 mmol, m.w.=198.22, yield 96.8%) of the desired product (5) as an oil.

$^1$H NMR (270 MHz, CDCl$_3$, TMS): δ1.32 (t, J=6.8 Hz, 7.3 Hz, 3H), 1.80 to 1.88 (tt, J=3.4 Hz, 3.9 Hz, 1H), 2.85 to 2.96 (m, 1H), 4.20 (q, 2H), 5.50 to 5.56 (m, 2H), 6.13 (t, J=5.9 Hz, 6.3 Hz, 2H) ppm

Example 6

Synthesis of (1S, 4R)-cis-1-o-bromophenoxy-4-acetoxy-2-cyclopentene (6)

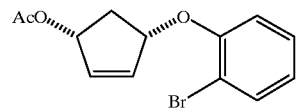

(6)

A 20 mL round-bottom flask was charged with 453.8 mg (2.29 mmol, m.w.=198.22) of (1S, 4R)-cis-1-ethoxycarbonyloxy-4-acetoxy-2-cyclopentene (5) and evacuated, followed by purging with argon. The compound was then dissolved in THF (6.5 mL) under nitrogen and 638 µL (4.58 mmol, m.w.=101.19, d=0.726) of triethylamine and 531 µL (4.58 mmol, m.w.=173.01, d=1.492) of o-bromophenol were added dropwise to the resulting solution at −20° C. A THF (1 mL) solution of 55.32 mg (0.0573 mmol, m.w.=966.22) of Pd$_2$(dba)$_3$/CHCl$_3$ complex and 120.13 mg (0.458 mmol, m.w.=262.29) of triphenylphosphine, prepared in a separate 10 mL round-bottom flask, was added and the mixture was stirred at room temperature for 3.5 hrs. The reaction was then quenched with a saturated aqueous solution (7 mL) of sodium hydrogen carbonate at −10° C. Progress of the reaction was checked by TLC (hexane/ethyl acetate=3/1, Rf of the objective compound=0.58, Rf of the starting material=0.49). After the solvent was removed in vacuo, 6 mL of water was added and the resulting mixture was extracted with ether (15 mL×4). The organic layer was dried over anhydrous sodium sulfate and filtrated, followed by concentration in vacuo. Purifrication on silica gel column chromatography (SiO$_2$=40 g, eluent: hexane/ethyl acetate=15/1) afforded 581.2 mg (1.96 mmol, m.w.=297.16, yield 85.4%) of the desired product (6) as an oil.

$^1$H NMR (270 MHz, CDCl$_3$, TMS): δ1.93 to 2.02 (tt, J=3.9 Hz, 4,4 Hz, 1H), 2.07 (s, 3H), 2.95 to 3.05 (m 1H), 5.15 (brd, 1H), 5.58 (brd, 1H), 6.13 (d, J=1.0 Hz, 1H), 6.27 (d, J=1.5 Hz, 1H), 6.85 (t, J=7.3 Hz, 7.8 Hz, 1H), 6.96 (d, J=8.5 Hz, 1H), 7.25 (t, J=6.6 Hz, 8.5 Hz, 1H), 7.55 (d, J=7.8 Hz, 1H) ppm IR (NaCl): 3454, 3068, 2937, 1734, 1580, 1475, 1439, 1370, 1239, 1039, 1023, 905, 753 cm$^{-1}$ Example 7

Synthesis of (1S, 4R)-cis-1-o-bromophenoxy-2-cyclopentene-4-ol (7)

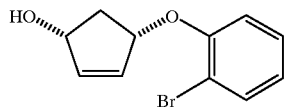
(7)

To a 10 mL round-bottom flask, 580.6 mg (1.954 mmol, m.w.=297.15) of (1S, 4R)-cis-o-bromophenoxy-4-acetoxy-2-cyclopentene (6) was added and dissolved in ethanol (5 mL). 3.37 mL of 2N aqueous solution of sodium hydroxide (6.74 mmol, m.w.=40.0) was added and stirred overnight at room temperature. Progress of the reaction was checked by TLC (hexane/ethyl acetate=1/1, Rf of the objective compound=0.64, Rf of the starting material=0.89). After the solvent was removed in vacuo, water (5 mL) was added to the residue and extracted with ether(20 mL×6). The organic layer was dried over anhydrous sodium sulfate and filtrated, followed by concentration in vacuo. Purification on silica gel column chromatography (SiO$_2$=40 g, eluent: hexane/ethyl acetate=25/1) afforded 348.2 mg (1.456 mmol, m.w.= 251.11, yield 71.0%) of the desired product (7) as an oil.

$^1$H NMR (270 MHz, CDCl$_3$, TMS): δ1.71 (J=9.8 Hz, 1H), 1.87 to 1.95 (tt, J=3.4 Hz, 3.9 Hz, 1H), 2.78 to 2.88(m, 1H), 4.72. (brd, 1H), 5.14 (brd, 1H), 6.20 (dd, J=5.4 Hz, 7.8 Hz, 2H), 6.85 (t, J=6.4 Hz, 7.8 Hz, 1H), 6.96 (d, J=6.8 Hz, 1H), 7.25 (t, J=8.0 Hz, 8.3 Hz, 1H), 7.55 (d, J=7.8 Hz, 1H) ppm 13C NMR (67.9 MHz, CDCl$_3$): δ42.2, 76.0, 82.6, 114.1, 116.1, 129.4, 133.6, 134.6, 139.9, 155.5 ppm IR(NaCL): 3378, 3067, 2895, 1580, 1474, 1363, 1279, 1242, 1059, 1026, 994, 752 cm$^{-1}$ $[a]_D^{21}$ −50.80° (c 1.28, CHCl$_3$)

Elementary analysis for C$_{11}$H$_{11}$O$_2$Br (F.W. 255.11) Theoretical (%) C: 50.02, H: 4.58 (0.5H$_2$O) Found (%) C: 50.12, H: 4.63

Example 8

Synthesis of (1S, 4R)-cis-1-o-bomophenoxy-4-benzyloxy-2-cyclopentene (8)

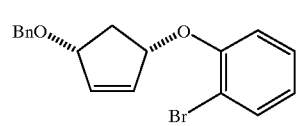
(8)

A 30 mL round-bottom flask was charged with 314 mg (1.31 mmol, m.w.=239.11) of (1S, 4R)-cis-1-o-bromophenoxy-2-cyclopentene-4-ol (7) and evacuated, followed by purging with argon. The compound was dissolved in dimethoxyethane (5.0 mL) under nitrogen, and the solution of 338.11 mg (7.04 mmol, m.w.=24.0, 50% by volume) of sodium hydride in dimethoxyethane (5 mL) was added. After bubbling was stopped, 1.56 mL of benzyl bromide 1.40 mL (11.74 mmol, m.w.=171.04, d=1.438) was added dropwise and the mixture was stirred at room temperture for 5 hrs. Progress of the reaction was checked by TLC (hexane/ethyl acetate=6/1, Rf of the objective compound=0.80, Rf of the starting material=0.16). The reaction was quenched with 5 mL of water and the solvent was removed in vacuo and the residue was extracted with ether (20 mL×2). The organic layer was dried over anhydrous sodium sulfate and filtrated, followed by concentration in vacuo. Purification on silica gel column chromatography (SiO$_2$=25 g, eluent: hexane→hexane/ethyl acetate=1/1) afforded 371.4 mg (1.13 mmol, m.w.=329.24, yield 96.51%) of the desired product (8) as an oil.

$^1$H NMR (270 MHz, CDCl$_3$, TMS): δ1.987 to 2.07 (tt, J=4.4 Hz, J=4.9 Hz, 1H), 2.83 to 2.95 (m, J=6.8 Hz, 7.3 Hz, 1H), 4.56 (d, J=2.4 Hz, 2H), 4.59 (m, 1H), 5.14 (m, 1H), 6.19 (s, 2H), 6.84 (t, J=7.3 Hz, 7.8 Hz, 1H), 6.93 (d, J=6.8 Hz, 1H), 7.21 to 7.36 (m 6H), 7.54 (d, J=7.8 Hz, 1H) ppm Example 9

Synthesis of (3aS, 8bS)-3a, 8b-cis-dihydro-3H-cyclopenta[b]benzofuran (9)

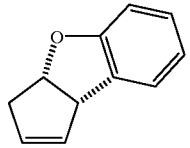
(9)

A Schrenk tube was charged with 127.8 mg (0.38 mmol, m.w.=329.24) of (1S, 4R)-cis-1-o-bromophenoxy-4-benzyloxy-2-cyclopentene (8) and evacuated, followed by purging with argon. THF (2 mL) was added and the solution was stirred at room temperature under nitrogen. The solution was then cooled to −78° C. or less and 0.278 mL (0.42 mmol, 1.51N hexane solution) of n-BuLi was slowly added with stirring. The reaction mixture was warmed to 0° C. within 1.5 hr (temperature increment of 10° C. in about 13 minutes). Progress of the reaction was checked by TLC (hexane/ether=10/1, Rf of the objective compound=0.68, Rf of the starting material=0.32, TLC plate: Merck 5715). The reaction was quenched with 4 mL of water and the resulting mixture was extracted with ether (7 mL×2). The organic layer was dried over anhydrous sodium salfate and filtrated, followed by concentration in vacuo. Purification on silica gel columun chromatography (SiO$_2$=4 g, eluent: hexane/ether=100/1) afforded 40.5 mg (0.26 mmol, m.w.=158.2, yield 67.4%) of the cyclization product (9) as an oil. The optical yield of cyclization product (9) was determined to 100%ee of S-configuration by chiral gas column chromatography (chiraldex G-TA30 m, column temperature=110° C., injection temperature 135° C., detection temperature=135° C., He pressure=1.5 atm).

$^1$H NMR (270 MHz, CDCl$_3$, TMS): δ2.80 (dd, J=1.5 Hz, 2.0 Hz, 1H), 2.87 (dd, J=1.5 Hz, 6.1 Hz, 1H), 4.37 Hz (d, J=8.7 Hz, 1H), 5.43 (m 1H), 5.76 (s, 2H), 6.73 to 7.21 (m, 4H) ppm Example 10

Synthesis of (1R, 4R)-trans-1-phenoxy-4-acetoxy-2-cyclopentene (10)

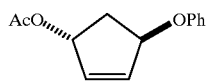

(10)

A 50 mL round-bottom flask was charged with 400 mg (2.81 mmol, m.w.=142.16) of commercially available (1S, 4R)-cis-4-acetoxy-2-cyclopentene-1-ol and 2.210 g (8.43 mmol, m.w.=262.29) of triphenylphosphine and evacuated, followed by purging with argon. The compounds were dissolved in benzene (7 mL) under nitrogen. A solution of 528.9 mg (5.62 mmol, m.w.=94.11) of phenol and 1.327 mL (8.43 mmol, m.w.=174.16, d=1.106) of diethyl azodicarboxylate dissolved in benzene (3 mL) were added dropwise at 4° C. and the mixture wad stirred for 4 hrs. Progress of the reaction was checked by TLC (hexane/ethyl acetate=3/1, Rf of the objective compound=0.70, Rf of the starting material=0.12, TLC plate: Merck 5715). The reaction was quenched with water (8 mL) and the solvent was removed in vacuo. The residue was extracted with ether (20 mL×3). The organic layer was washed with an aqueous solution (5 mL) of oxalic acid and a saturated aqueous solution (5 mL) of sodium hydrogen carbonate. The organic layer was further washed with 0.5N aqueous sodium hydroxide solution (4 mL×4) by cooling with ice and then washed with a saturated aqueous solution (5 mL) of sodium hydrogen carbonate. The organic layer was dried over anhydrous sodium sulfate and filtrated, followed by concentration in vacuo. Purification on silica gel column chromatography (SiO$_2$=25 g, eluent: hexane/ether=10/1) afforded 446.2 mg (2.04 mmol, m.w.=218.26, yield 72.8%) of the desired product (10) as an oil.

$^1$H NMR (270 MHz, CDCl$_3$, TMS): δ2.06 (s, 3H), 2.26 to 2.44 (m, 2H), 5.47 (m, 1H), 5.84 (m 1H), 6.16 (m 1H), 6.26 (m, 1H), 6.85 (d, J=8.8 Hz, 2H), 6.92 (t, J=6.3 Hz, 6.9 Hz, 1H), 7.25 (t, J=6.3 Hz, 7.3 Hz, 2H) ppm IR (neat): 3437, 3068, 2944, 1734, 1581, 1475, 1441, 1369, 1240, 1036, 750 cm$^{-1}$ Example 11

Synthesis of (1R, 4R)-trans-1-phenoxy-2-cyclopentene-4-ol (11)

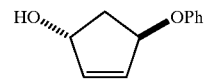

(11)

To a 10 mL round-bottom flask, 428.3 mg (1.962 mmol, m.w.=218.26) of (1R, 4R)-trans-1-phenoxy-4-acetoxy-2-cyclopentene (10) was added and dissolved in ethanol (5 mL). 4 mL of 2N aqueous solution of sodium hydroxide (8 mmol, m.w.=40.0) was added and the mixture was stirred at room temperature for 2.5 hrs. Progress of the reaction was checked by TLC (hexane/ethyl acetate=1/1, Rf of the objective compound=0.66, Rf of the starting material=0.90, TLC plate: Merck 5715). After the solvent was removed in vacuo, water (5 mL) was added to the residue and the resulting mixture was extracted with ether (30 mL×2). The organic layer was dried over anhydrous sodium sulfate and filtrated, followed by concentration in vacuo. 321.8 mg (1.826 mmol, m.w.=176.22, yield 93.1%) of the desired product (11) was obtained as a white solid.

$^1$H NMR (270 MHz, CDCl$_3$, TMS): δ1.62 (d, J=5.4 Hz, 1H), 2.15 to 2.24 (td, J=3.4 Hz, 3.4 Hz, 1H), 2.32 to 2.41 (td, J=2.9 Hz, 3.4 Hz, 1H), 5.13 (m, 1H), 5.50 (m, 1H), 6.18 (dd, J=6.8 Hz, 6.9 Hz, 2H), 6.95 (t, J=7.3 Hz, 7.3 Hz, 1H), 6.88 (d, J=8.9 Hz, 2H), 7.29 (t, J=6.3 Hz, 7.3 Hz, 2H) ppm IR (KBr): 3369, 2910, 1591, 1492, 1365, 1295, 1229, 1058, 756 cm$^{-1}$ $[\alpha]_D^{25}$ +153° (C 1.15, CHCl$_3$)

Elementary analysis for C$_{11}$H$_{12}$O$_2$ (F.W. 176.215) Theoretical (%) C: 74.22, H: 6.91 (0.1 H$_2$O) Found (%) C: 74.13, H: 6.94 mp=78° C.

Example 12

Synthesis of (1R, 4S)-cis-1-phenoxy-4-o-bromophenoxy-2-cyclopentene (12)

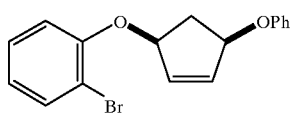

(12)

A 10 mL round-bottom flask was charged with 141 mg (0.80 mmol, m.w.=176.22) of (1R, 4R)-trans-1-phenoxy-2-cyclopentene-4-ol (11) and 629.5 mg (2.40 mmol, m.w.=262.29) of triphenylphosphine and evacuated, followed by purging with argon. The compounds were dissolved in benzene (4 mL) under nitrogen and 185.53 μL (1.60 mmol, m.w.=173.01, d=1.492) of o-bromophenol and 377.92 μL (2.40 mmol, m.w.=174.16, d=1.106) of diethyl azodicarboxylate were added dropwise at 4° C. and the mixture was stirred for 2 hrs. Progress of the reaction was checked by TLC (hexane/ether=3/1, Rf of the objective compound=

0.61, Rf of the starting material=0.08, TLC plate: Merck 5715). The reaction was quenched with water (5 mL) and the solvent was removed in vacuo. The residue was extracted with ether (15 mL×2). The organic layer was washed with an aqueous solution (5 mL) of oxalic acid and a saturated aqueous solution (5 mL) of sodium hydrogen carbonate. The organic layer was further washed with 0.5N aqueous sodium hydroxide solution (4 mL) by cooling with ice and then washed with a saturated-aqueous solution (5 mL) of sodium hydrogen carbonate. The organic layer was dried over anhydrous sodium sulfate and filtrated, followed by concentration in vacuo. Purification on silica gel column chromatography (SiO$_2$=30 g, eluent: hexane/ether=10/1) afforded 223.3 mg (0.67 mmol, m.w.=331.21, yield 84.3%) of the desired product (12) as an white solid.

$^1$H NMR (270 MHz, CDCl$_3$, TMS): δ2.08 to 2.22 (tt, J=4.4 Hz, 4,4 Hz, 1H), 3.04 to 3.15 (tt, J=6.8 Hz, 7.3 Hz, 1H), 5.23 (m, 2H), 6.30 (dd, J=6.8 Hz, 6.9 Hz, 2H), 6.85 (t, J=6.4 Hz, 7.3 Hz, 1H), 6.92 (m, 4H), 7.25 (m, 3H), 7.55 (d, J=7.3 Hz, 1H) ppm IR (KBr): 3860, 3757, 3067, 2897, 2400, 1589, 1478, 1442, 1374, 1342, 1278, 1237, 1176, 1122, 1081, 1033, 995, 913 cm$^{-1}$

Example 13

Synthesis of (1R, 4S)-cis-1-phenoxy-4-(2, 4, 6-tribromo-phenoxy)-2-cyclopentene (13)

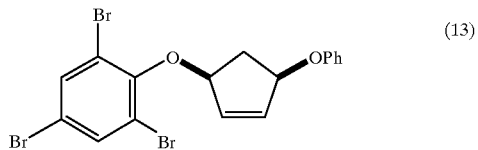

(13)

A 10 mL round-bottom flask was charged with 141 mg (0.80 mmol, m.w.=176.22) of (1R, 4R)-trans-1-phenoxy-2-cyclopentene-4-ol (11) and 629.5 mg (2.40 mmol, m.w.=262.29) of triphenylphosphine and evacuated, followed by purging with argon. The compounds were dissolved in benzene (4 mL) under nitrogen. 529.28 mg (1.60 mmol, m.w.=330.80) of 2,4,6-tribromophenol and 377.92 μL (2.40 mmol, m.w.=74.16, d=1.106) of diethyl azodicarboxylate were added dropwise at 9° C. and the mixture was stirred for 2 hrs. Progress of the reaction was checked by TLC (hexane/ether=3/1, Rf of the objective compound=0.71, Rf of the starting material=0.06, TLC plate: Merck 5715). The reaction was quenched with water (5 mL) and the solvent was removed in vacuo. The residue was extracted with ether (15 mL×2). The organic layer was washed with an aqueous solution (5 mL) of oxalic acid and a saturated aqueous solution (5 mL) of sodium hydrogen carbonate. The organic layer was further washed with 0.5N aqueous sodium hydroxide solution (4 mL) by cooling with ice and then washed with a saturated aqueous solution (5 mL) of sodium hydrogen carbonate. The organic layer was dried over anhydrous sodium sulfate and filtrated, followed by concentration in vacuo. Purification on silica gel column chromatography (SiO$_2$ =25 g, eluent: hexane→hexane/methylene chloride=3/1) afforded 342.7 mg (0.70 mmol, m.w.=489.0, yield 87.6%) of the desired product (13) as a white solid.

$^1$H NMR (270 MHz, CDCl$_3$, TMS): δ2.37 to 2.45 (tt, J=4.4 Hz, 4.9 Hz, 1H), 2.99 to 3.09 (tt, J=7.3 Hz, 7.8 Hz, 1H), 5.15 (m, 1H), 5.87 (m, 1H), 6.24 (d, J=6.4 Hz, 1H), 6.34 (d, J=5.4 Hz, 1H), 6.97 (m, 3H), 7.28 (t, J=7.8 Hz, 8,3 Hz, 1H), 7.70 (s, 2H) ppm IR (KBr): 3865, 3629, 2924, 2856, 2375, 1593, 1550, 1488, 1440, 1373, 1236, 1073, 1023, 967, 865, 743, 690 cm$^{-1}$

Example 14

Synthesis of (3aS, 8bS)-3a, 8b-cis-dihydro-3H-cyclopenta[b]benzofuran (9)

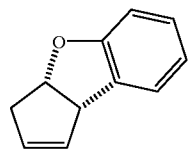

(9)

A Schrenk tube was charged with 65.0 mg (0.196 mmol, m.w.=331.21) of (1R, 4S)-cis-1-phenoxy-4-o-bromophenoxy-2-cyclopentene (12) and evacuated, followed by purging with argon. THF (1.2 mL) was added and the solution was stirred at room temperature under nitrogen. The solution was then cooled to −78° C. or less and 0.144 mL (0.216 mmol, 1.50N hexane solution) of n-BuLi was slowly added with stirring. The reaction mixture was warmed to 0° C. within 1.5 hr (temperature increment of 10° C. in about 13 minutes). Progress of the reaction was checked by TLC (hexane/ether=10/1, Rf of the objective compound=0.68, Rf of the starting material=0.32, TLC plate: Merck 5715). The reaction was quenched with 3 mL of water and the resulting mixture was extracted with ether (10 mL×2). The organic layer was dried over anhydrous sodium salfate and fitrated, followed by concentration in vacuo. Purification on silica gel columun chromatography (SiO$_2$=4 g, eluent: hexane/ether=100/1) afforded 17.0 mg (0.11 mmol, m.w.=158.2, yield 54.8%) of the cyclization product (9) as an oil. The optical yield of cyclization product (9) was determined to 99.3%ee of S-configuration by chiral gas column chromatography (chiraldex G-TA30 m, column temperature=110° C., injection temperature=135° C., detection temperature=135° C., He pressure=150 kPa).

$^1$H NMR (270 MHz, CDCl$_3$, TMS): δ2.80 (dd, J=1.5 Hz, 2.0 Hz. 1H), 2.87 (dd, J=1.5 Hz, 6.1 Hz, 1H), 4.37 (d, J=8.7 Hz, 1H), 5.43 (m, 1H), 5.76 (s, 2H), 6.73 to 7.21 (m, 4H) ppm

Example 15

Synthesis of (1S, 4R)-cis-1-phenoxy-4-acetoxy-2-cyclopentene (14)

(14)

A 20 mL round-bottom flask was charged with 263.2 mg (1.23 mmol, m.w.=214.22) of (1S, 4R)-cis-1- ethoxycarbonyloxy-4-acetoxy-2-cyclopentene (5) and evacuated, followed by purging with argon. The compound was dissolved in THF (1.5 mL) under nitrogen and 231.51 mg (2.46 mmol, m.w.=94.11) of phenol dissolved in THF (1 mL) was added dropwise to the resulting mixture at 0° C. A THF (2 mL) solution of 118.8 mg (0.123 mmol, m.w.= 966.22) of Pd$_2$(dba)$_3$/CHCl$_3$ complex and 258.10 mg (0.984 mmol, m.w.=262.29) of triphenylphosphine, prepared in a separate 10 mL round-bottom flask, was added and the the mixture was stirred at 8° C. for 4 hrs. The reaction was quenched with a saturated aqueous solution (3 mL) of sodium hydrogen carbonate. Progress of the reaction was checked by TLC (hexane/ethyl acetate=3/1, Rf of the objective compound=0.58, Rf of the starting material=0.17, TLC plate: Merck 5715). After the solvent was removed in vacuo, 6 mL of water was added and the resulting mixture was extracted with ether (20 mL). The organic layer was washed with 0.5N aqueous sodium hydroxide solution (2 mL×2) by cooling with ice, followed by washing with a saturated aqueous solution (5 mL) of sodium hydrogen carbonate. The organic layer was dried over anhydrous sodium sulfate and filtrated, followed by concentration in vacuo. Purification on silica gel column chromatography(SiO$_2$=20 g, eluent: hexane/methylene chloride=2/1) afforded 214.8 mg (0.98 mmol, m.w.=218.26, yield 80.0%) of the desired product (14) as a yellow solid. Also, 29.2 mg of the staring material (5) was recovered.

$^1$H NMR (270 MHz, CDCl$_3$, TMS): δ1.85 to 1.93 (tt, J=3.9 Hz, 3.9 Hz, 1H), 2.05 (s, 3H), 2.92 to 3.03 (tt, J=7.3 Hz, 7.4 Hz, 1H), 5.16 (m, 1H), 5.61 (m, 1H), 6.13 (m, 1H), 6.24 (m, 1H), 6.92 (d, J=7.8 Hz, 2H), 6.94 (t, J=5.9 Hz, 7.3 Hz, 1H), 7.25 (t, J=7.3 Hz, 7.8 Hz, 2H) ppm IR (KBr): 3066, 3039, 2944, 1732, 1599, 1586, 1495, 1432, 1367, 1290, 1228, 1174, 1078, 1043, 965, 884, 856, 818, 692 cm$^{-1}$ Example 16

Synthesis of (1S, 4R)-cis-1-phenoxy-2-cyclopentene-4-ol (15)

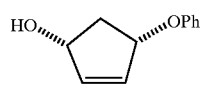

(15)

To a 20 mL round-bottom flask, 363.98 mg (1.67 mmol, m.w.=218.26) of (1S, 4R)-cis-1-phenoxy-4-acetoxy-2-cyclopentene (14) was added and dissolved in ethanol(5 mL). 3.34 mL of 2N aqueous solution of sodium hydroxide (6.68 mmol, m.w.=40.0) was added and the mixture was stirred overnight at room temperature. Progress of the reaction was checked by TLC (hexane/ethyl acetate=1/1, Rf of the objective compound=0.56, Rf of the starting material= 0.89, TLC plate: Merck 5715). After the solvent was removed in vacuo, water (5 mL) was added to the residue and extracted with ether (20 mL×3). The organic layer was dried over anhydrous sodium sulfate and filtrated, followed by concentration in vacuo. Purification on silica gel column chromatography (SiO$_2$=20 g, eluent: hexane/ethyl acetate= 3/1) afforded 292.5 mg (1.66 mmol, m.w.=176.22, yield 99.4%) of the desired product (15) as an oil.

$^1$H NMR (270 MHz, CDCl$_3$, TMS): δ1.64 (d, J=9.3 Hz, 1H), 1.76 to 1.85 (tt, J=3.4 Hz, 3.9 Hz, 1H), 2.83 to 2.93 (tt, J=6.8 Hz, 7.3 Hz, 1H), 4.75 (m, 1H), 5.13 (m, 1H), 6.20 (t, J=7.3 Hz, 7.3 Hz, 2H), 6.93 (d, J=8.8 Hz, 2H), 6.98 (t, J=6.3 Hz, 8.3 Hz, 1H), 7.25 (t, J=7.8 Hz, 7.8 Hz, 2H) ppm IR (NaCl): 3230, 2977, 2879, 1598, 1493, 1362, 1299, 1250, 1170, 1088, 1071, 1036, 1004, 878, 814, 753, 690 cm$^{-1}$ $[α]_D^{25}$ +11.1° (c 0.90, CHCl$_3$)

Elementary assay for C$_{11}$H$_{12}$O$_2$ (F.W. 176.215) Theoretical(%) C: 74.98, H: 6.86 Found: (%) C: 74.73, H: 6.91

Example 17

Synthesis of (1S, 4S)-trans-1-phenoxy-4-o-bromophenoxy-2-cyclopentene (16)

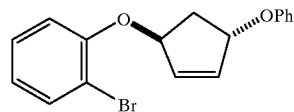

(16)

A 20 mL round-bottom flask was charged with 132 mg (0.75 mmol, m.w.=176.22) of (1S, 4R)-cis-1-phenoxy-2-cyclopentene- 4-ol (15) and 590.2 mg (2.25 mmol, m.w.= 262.29) of triphenylphosphine and evacuated, followed by purging with argon. The compounds were dissolved in benzene (2 mL) under nitrogen. 173.9 μL (1.50 mmol, m.w.=173.01, d =1.492) of o-bromophenol and 1.02 mL (2.25 mmol, m.w.=174.16, d=0.96, 40% solution in toluene) of diethyl azodicarboxylate were added dropwise at 4° C. and the mixture was stirred for 2 hrs. Progress of the reaction was checked by TLC (hexane/ether=3/1, Rf of the objective compound=0.58, Rf of the starting material=0.04, TLC plate: Merck 5715). The reaction was quenched with water (8 mL) and the solvent was removed in vacuo. The residue was extracted with ether (20 mL×2). The organic layer was washed with an aqueous solution (5 mL) of oxalic acid and a saturated aqueous-solution (10 mL) of sodium hydrogen carbonate. The organic layer was further washed with 0.5N aqueous sodium hydroxide solution (2.5 mL×2) by cooling with ice and then washed with a saturated aqueous solution (10 mL) of sodium hydrogen carbonate. The organic layer was dried over anhydrous sodium sulfate and filtrated, followed by concentration in vacuo. Purification on silica gel column chromatography (SiO$_2$=15 g, eluent: hexane/methylene chloride=4/1) afforded 202.8 mg (0.61 mmol, m.w.=331.21, yield 81.6%) of the desired product (16) as a white solid.

$^1$H NMR (270 MHz, CDCl$_3$, TMS): δ2.42 to 2.52 (m, 2H), 5.57 (m, 2H), 6.34 (t, J=6.8 Hz, 6.9 Hz, 1H), 6.82 to 6.99 (m, 5H), 7.22 to 7.33 (m, 3H), 7.56 (d, J=7.8 Hz, 1H) ppm IR (KBr): 3654, 3062, 2925, 2400, 1585, 1478, 1442, 1371, 1280, 1233, 1174, 1126, 1079, 1051, 1033, 1007, 951, 881, 798, 751, 692, 664 cm$^{-1}$

Example 18

Synthesis of (1S, 4S)-trans-1-phenoxy-4-(2,4,6-tribromophenoxy)-2-cyclopentene (17)

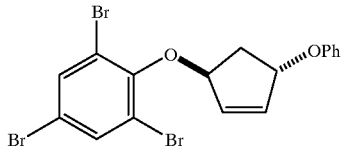

(17)

A 10 mL round-bottom flask was charged with 125 mg (0.71 mmol, m.w.=176.22) of (1S, 4R)-cis-1-phenoxy-2-cyclopentene-4-ol (15) and 558.7 mg (2.13 mmol, m.w.=262.29) of triphenylphosphine and evacuated, followed by purging with argon. The compounds were dissolved in benzene (4 mL) under nitrogen. 469.74 mg (1.42 mmol, m.w.=330.80) of 2,4,6-tribromophenol and 0.97 mL (2.13 mmol, m.w.=74.16, d=0.96, 40% toluene solution) of diethyl azodicarboxylate were added dropwise at 8° C. and the mixture was stirred for 2 hrs. Progress of the reaction was checked by TLC (hexane/ether=3/1, Rf of the objective compound=0.76, Rf of the starting material=0.04, TLC plate: Merck 5715). The reaction was quenched with water (5 mL) and the solvent was removed in vacuo. The residue was extracted with ether (15 mL×2). The organic layer was washed with an aqueous solution (3 mL) of oxalic acid and a saturated aqueous solution (5 mL) of sodium hydrogen carbonate. The organic layer was further washed with 0.5N aqueous sodium hydroxide solution (3 mL) by cooling with ice and then washed with a saturated aqueous solution (3 mL) of sodium hydrogen carbonate. The organic layer was dried over anhydrous sodium sulfate and filtrated, followed by concentration in vacuo. Purification on silica gel column chromatography (SiO$_2$=20 g, eluent : hexane/methylene chloride=3/1) afforded 318.02 mg (0.65 mmol, m.w.=489.0, yield 91.6%) of the desired product (17) as a white solid.

$^1$H NMR (270 MHz, CDCl$_3$, TMS): δ2.31 to 2.40 (td, J=2.8 Hz, 3.4 Hz, 1H), 2.75 to 2.83 (td, J=2.4 Hz, 2.9 Hz, 1H), 5.58 (m, 1H), 5.63 (m, 1H), 6.30 (m, 2H), 6.92 (d, J=7.8 Hz, 2H), 6.96 (t, J=4.9 Hz, 8.3 Hz, 1H), 7.25 (t, J=8.3 Hz, 9.1 Hz, 2H), 7.68 (s, 2H) ppm IR (KBr): 3856, 3753, 3068, 2944, 1600, 1587, 1561, 1538, 1496, 1440, 1371, 1245, 1078, 1039, 1023, 959, 880, 857, 797, 748, 735, 693 cm$^{-1}$

Example 19

Synthesis of (3aS, 8bS)-3a,8b-cis-dihydro-3H-cyclopenta[b]benzofuran (9)

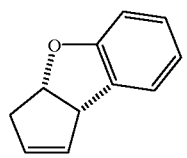

(9)

A Schrenk tube was charged with 132.48 mg (0.40 mmol, m.w.=331.21) of (1S, 4S)-trans-1-phenoxy-4-o-bromophenoxy-2-cyclopentene (16) and evacuated, followed by purging with argon. THF (2 mL) was added and the solution was stirred at room temperature under nitrogen. The solution was then cooled to −78° C. or less and 0.293 mL (0.44 mmol, 1.50N hexane solution) of n-BuLi was slowly added with stirring. The reaction mixture was warmed to 0° C. within 1.5 hr (temperature increment of 10° C. in about 13 minutes). Progress of the reaction was checked by TLC (hexane/ether=10/1, Rf of the objective compound=0.68, Rf of the starting material=0.32, TLC plate: Merck 5715). The reaction was quenched with 3 mL of water and the resulting mixture was extracted with ether (10 mL×2). The organic layer was dried over anhydrous sodium salfate and filtrated, followed by concentration in vacuo. Purification on silica gel columun chromatography (SiO$_2$=4 g, eluent: hexane/ether=100/1) afforded 34.6 mg (0.22 mmol, m.w.=158.2, yield 54.7%) of the cyclization product (9) as an oil. The optical yield of cyclization product (9) was determined to 99.3%ee of S-configuration by chiral gas column chromatography (chiraldex G-TA30 m, column temperature=110° C., injection temperature=135° C., detection temperature=135° C., He pressure=150 kPa).

$^1$H NMR (270 MHz, CDCl$_3$, TMS): δ2.80 (dd, J=1.5 Hz, 2.0 Hz, 1H), 2.87 (dd, J=1.5 Hz, 6.1 Hz, 1H), 4.37 (d, J=8.7 Hz, 1H), 5.43 (m, 1H), 5.76 (s, 2H), 6.73 to 7.21 (m, 4H) ppm

Example 20

Synthesis of (3aS, 8bS)-3a,8b-cis-dihydro-5,7-dibromo-3H-cyclopenta[b]dibromobenzofuran (18)

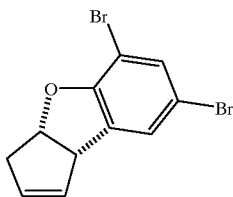

(18)

A Schrenk tube was charged with 122.3 mg (0.25 mmol, m.w.=489.0) of (1S, 4S)-trans-1-phenoxy-4-(2,4,6-tribromophenoxy)-2-cyclopentene (17) and evacuated, followed by purging with argon. THF (2 mL) was added and the mixture was stirred at room temperature under nitrogen. 0.248 mL (0.375 mmol, 1.51N THF solution) of n-butylmagnesium bromide was slowly added with stirring at room temperature for 0.5 hr, followed by adding 2.39 mg (0.0125 mmol, m.w.=190.45, 5 mol %) of copper iodide and stirred for 0.5 hr. Progress of the reaction was checked by TLC (hexane/ether=6/1, Rf of the objective compound=0.57, Rf of the starting material=0.83, TLC plate: Merck 5715). The reaction was quenched with 3 mL of water and the resulting mixture was extracted with ether (20 mL×2). The organic layer was dried over anhydrous sodium salfate and filtrated, followed by concentration in vacuo. Purification on silica gel columun chromatography (SiO$_2$=5 g, eluent: hexane/ether=100/1) afforded 53.6 mg (0.17 mmol, m.w.=315.99, yield 67.8%) of the cyclization product (18) as a white solid.

$^1$H-NMR (270 MHz, CDCl$_3$, TMS): δ2.89 (m, 2H), 4.48 (m, 2H), 5.60 (m, 1H), 5.80 (m, 2H), 7.25 (d, J=2.0 Hz, 1H, 7.39 (d, J=2.0 Hz, 1H) ppm mp=113° C.

$[\alpha]_D^{25}$: −147.3° (c 1.00, CHCl$_3$)

Example 21

Synthesis of (1S, 4S)-trans-1-phenoxy-4-o-bromophenoxy-2-cyclopentene (16)

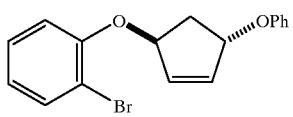
(16)

A 10 mL round-bottom flask was charged with 15.6 mg (0.062 mmol, m.w.,=251.11) of (1S, 4R)-cis-1-o-bromophenoxy-2-cyclopentene-4-ol (7) and 48.79 mg (0.186 mmol, m.w.=262.29) of triphenylphosphine and evacuated, followed by purging with argon. The compounds were dissolved in benzene (1 mL) under nitrogen and 11.7 mg (0.124 mmol, m.w.=94.11) of phenol and 84.4 μL (0.186 mmol, m.w.=174.16, d=0.96, 40% toluene solution) of diethyl azodicarboxylate were added dropwise at 4° C. and the mixture was stirred for 2 hrs. Progress of the reaction was checked by TLC (hexane/ether=5/1, Rf of the objective compound=0.68, Rf of the starting material=0.03, TLC plate: Merck 5715). The reaction was quenched with water (2 mL) and the solvent was removed in vacuo. The residue was extracted with ether (5 mL×2). The organic layer was washed with an aqueous solution (1 mL) of oxalic acid and a saturated aqueous solution (4 mL) of sodium hydrogen carbonate. The organic layer was further washed with 0.5N aqueous sodium hydroxide solution (1 mL×2) by cooling with ice and then washed with a saturated aqueous solution (3 mL) of sodium hydrogen carbonate. The organic layer was dried over anhydrous sodium sulfate and filtrated, followed by concentration in vacuo. Purification on silica gel column chromatography (SiO$_2$=15 g, eluent: hexane) afforded 17.1 mg (0.052 mmol, m.w.=331.21, yield 83.3%) of the desired product (16) as an white solid.

$^1$H NMR (270 MHz, CDCl$_3$, TMS): δ2.42 to 2.52 (m, 2H), 5.57 (m, 2H), 6.34 (t, J=6.8 Hz, 6.9 Hz, 1H), 6.82 to 6.99 (m, 5H), 7.22 to 7.33 (m, 3H), 7.56 (d, J=7.8 Hz, 1H) ppm IR (KBr): 3654, 3062, 2925, 2400, 1585, 1478, 1442, 1371, 1280, 1233, 1174, 1126, 1079, 1051, 1033, 1007, 951, 881, 798, 751, 692, 664 cm$^{-1}$ Example 22

Synthesis of (1S, 4R)-cis-1-o-bromophenoxy-2-cyclopentene-1-ol (19)

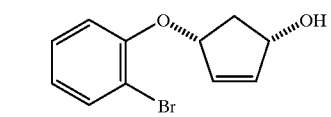
(19)

A 10 mL round-bottom flask was charged with 100 mg (0.70 mmol, m.w.=142.16) of commercially available (1S, 4R)-cis-4-acetoxy-2-cyclopentene-1-ol and evacuated, followed by purging with argon. The compound was then dissolved in THF (1.5 mL) under nitrogen and 294.4 μL (2.11 mmol, m.w.=101.19, d=0.726) of triethylamine and 244.9 μL (2.11 mmol, m.w.=173.01, d=1.492) of o-bromophenol were added dropwise to the resulting mixture at 10° C. The THF solution (0.5 mL) of 17.0 mg (0.0176 mmol, m.w.=966.22) of Pd$_2$(dba)$_3$/CHCl$_3$ complex and 37.0 mg (0.141 mmol, m.w.=262.29) of triphenylphosphine, prepared in a separate 10 mL round-bottom flask, was added and the mixture was stirred with at room temperature for 24 hrs. Progress of the reaction was checked by TLC (hexane/ethyl acetate=1/1, Rf of the objective compound=0.53, Rf of the starting material=0.28). The reaction was then quenched with a saturated aqueous solution (6 mL) of sodium hydrogen carbonate. The solvent was removed in vacuo and 8 mL of water was added and the resulting mixture was extracted with methylene chloride (20 mL×4). The organic layer was dried over anhydrous sodium sulfate and filtrated, followed by concentration in vacuo. Purifrication on silica gel column chromatography (SiO$_2$=11 g, eluent: hexane/ethyl acetate=7/1) afforded 84.4 mg (0.33 mmol, m.w.=255.11, yield 47.0%) of the desired product (19) as an oil.

$^1$H NMR (270 MHz, CDCl$_3$, TMS): δ1.78 (d, J=9.3 Hz, 1H), 1.87 to 1.95 (tt, J=3.4 Hz, 3.9 Hz, 1H), 2.78 to 2.89 (m, J=6.8 Hz, 7.3 Hz, 1H), 4.74 (brd, 1H), 5.13 (brd, 1H), 6.20 (m, 2H), 6.85 (t, j=7.3 Hz, 8.1 Hz, 1H), 6.96 (d, J=6.8 Hz, 1H), 7.25 (t, J=7.1 Hz, 8.6 Hz, 1H), 7.55 (d, J=7.5 Hz, 1H) ppm $^{13}$C NMR (67.9 MHz, CDCl$_3$): δ42.2, 76.0, 82.6, 114.1, 116.1, 123.3, 129.4, 133.6, 134.6, 139.9, 155.5 ppm IR (NaCl): 3352, 3065, 2896, 1580, 1473, 1363, 1277, 1241, 1170, 1058, 1026, 996, 750 cm$^{-1}$ $[\alpha]_D^{21}$ +51.0° (c 1.11, CHCl$_3$)

Elementary assay for C$_{11}$H$_{11}$O$_2$Br (F.W. 255.11) Theoretical(%) C: 50.02, H: 4.58 (0.5 H$_2$O) Found (%) C: 50.25, H: 4.51

Industrial Applicability

The present invention enables an optically active compound of cycloalkyl[b]benxofuran to be produced by using a readily available optically active starting material. The production process according to the present invention can exclude the needs of complicated optical resolution steps as well as enzyme reactions that require a large amount of solvents and long reaction time besides repeatability is hardly obtained, providing a very useful production process that can apply for not only laboratory preparations but also for industrial scale productions.

What is claimed is:

1. A process for producing an optically active compound cycloalkyl[b]benzofuran represented by the formula (IV), comprising:

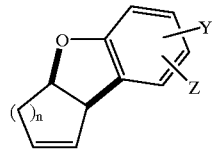
(IV)

converting a optically active compound represented by formula (III) as a starting material into a compound represented by formula (V) by a reaction using a transition metal, the Mitsunobu reaction, or a combination thereof, and cyclizing the compound represented by formula (V) using a metallic reagent or an organometallic reagent, (III)

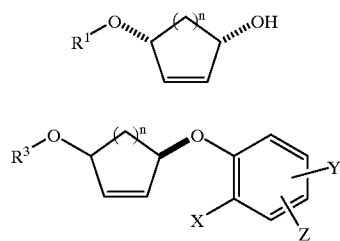

(V)

wherein, $R^1$ denotes an acyl group with a carbon number of 1 to 12, an aroyl group with a carbon number 7 to 15 or $CO_2R^2$ group, $R^2$ represents a linear or branched alkyl group with a carbon number of 1 to 12, a cycloalkyl group with a carbon number of 3 to 8, or an aryl group with a carbon number of 6 to 11, $R^3$ denotes a linear or branched alkyl group with a carbon number of 1 to 12, an aralkyl group with a carbon number of 7 to 12, a linear or branched alkylsulfonyl group with a carbon number of 1 to 12, an arylsulfonyl group with a carbon number of 6 to 12, or $R^5$, $R^5$ denotes an aryl group with a carbon number of 6 to 11, X denotes halogen, n is an integer in the range of 0 to 4, and Y and Z independently denote hydrogen, halogen, an alkyl group with a carbon number of 1 to 5, a cycloalkyl group with a carbon number of 3 to 8, a cycloalkylalkyl group with a carbon number of 4 to 9, a cycloalkenylalkyl group with a carbon number of 5 to 10, an aralkyl group with a carbon number of 7 to 12, an alkenyl group with a carbon number of 2 to 7, or an aryl group with a carbon number of 6 to 11.

2. A process for producing an optically active compound cycloalkyl[b]benzofuran represented by the formula (VI), comprising:

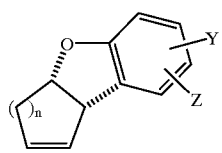
(VI)

converting a optically active compound represented by formula (III) as a starting material into a compound represented by formula (VII) by a reaction using a transition metal, the Mitsunobu reaction, or a combination thereof, and cyclizing the compound represented by formula (VII) using a metallic reagent or an organometallic reagent, (III)

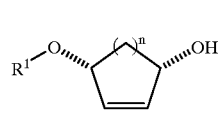

(VII)

wherein, $R^1$ denotes an acyl group with a carbon number of 1 to 12, an aroyl group with a carbon number 7 to 15 or $CO_2R^2$ group, $R^2$ represents a linear or branched alkyl group with a carbon number of 1 to 12, a cycloalkyl group with a carbon number of 3 to 8, or an aryl group with a carbon number of 6 to 11, $R^3$ denotes a linear or branched alkyl group with a carbon number of 1 to 12, an aralkyl group with a carbon number of 7 to 12, a linear or branched alkylsulfonyl group with a carbon number of 1 to 12, an arylsulfonyl group with a carbon number of 6 to 12, or $R^5$, $R^5$ denotes an aryl group with a carbon number of 6 to 11, X denotes halogen, n is an integer in the range of 0 to 4, and Y and Z independently denote hydrogen, halogen, an alkyl group with a carbon number of 1 to 5, a cycloalkyl group with a carbon number of 3 to 8, a cycloalkylalkyl group with a carbon number of 4 to 9, a cycloalkenylalkyl group with a carbon number of 5 to 10, an aralkyl group with a carbon number of 7 to 12, an alkenyl group with a carbon number of 2 to 7, or an aryl group with a carbon number of 6 to 11.

3. A process for producing cycloalkyl[b]benzofuran according to claims 1 or 2, wherein n in formula (I) to (VII) is 1.

* * * * *